United States Patent [19]

Webb

[11] Patent Number: 5,561,124
[45] Date of Patent: Oct. 1, 1996

[54] 17-α-ACYL STEROIDS WHICH INHIBIT 5-α-REDUCTASE

[76] Inventor: Robert L. Webb, SmithKline Beecham Corporation Corporate Intellectual Property-U.S., UW2220 P.O. Box 1539, King of Prussia, Pa. 19406-0939

[21] Appl. No.: 436,292

[22] PCT Filed: Nov. 18, 1993

[86] PCT No.: PCT/US93/11235

§ 371 Date: May 17, 1995

§ 102(e) Date: May 17, 1995

[87] PCT Pub. No.: WO94/11385

PCT Pub. Date: May 26, 1994

[30] Foreign Application Priority Data

Nov. 18, 1992 [GB] United Kingdom ............... 9224148

[51] Int. Cl.$^6$ ............... A61K 31/56; A61K 31/58; C07J 41/00; C07J 9/00
[52] U.S. Cl. ............... 514/169; 514/176; 514/177; 514/182; 514/284; 514/563; 546/77; 562/498; 552/502; 552/506; 552/521; 552/524; 552/540; 552/546; 552/548; 552/552; 552/553; 552/554; 552/556; 552/557; 552/558; 552/599; 552/600; 552/601; 552/606; 552/607; 552/610; 552/611
[58] Field of Search ............... 546/77; 562/498; 514/169, 176, 177, 182, 284, 563; 552/502, 506, 521, 524, 540, 546, 548, 552, 553, 554, 556, 557, 558, 599, 600, 601, 606, 607

[56] References Cited

U.S. PATENT DOCUMENTS

| | | |
|---|---|---|
| 4,377,584 | 3/1983 | Rasmusson et al. . |
| 4,970,199 | 11/1990 | Durette et al. . |
| 4,970,204 | 11/1990 | Holt et al. . |
| 5,100,917 | 3/1992 | Flynn et al. . |

OTHER PUBLICATIONS

J. Steroid Biochem, Molec. Biol. vol. 37, No. 4, pp. 575–579 1990.
J. Med. Chem. 33, pp. 943–950 1990.
J. Med. Chem. 33 pp. 937–942 1990.
J. of Chromatography, 631 (1993) 251–254.

*Primary Examiner*—Kimberly J. Prior
*Attorney, Agent, or Firm*—Wayne J. Dustman; Stephen Venetianer; Edward T. Lentz

[57] ABSTRACT

The invention relates to substituted 17α-acyl steroidal 5α-reductase inhibiting compounds. The invention also relates to pharmaceutical compositions containing these compounds and their use for reducing prostate size and treating prostate adenocarcinoma. Further, the invention describes a process for making these compounds by heating the corresponding substituted 17β-acyl steroid in a solvent, such as ethylene glycol or dimethyl sulfoxide (DMSO), in a base, such as sodium or potassium hydroxide.

18 Claims, No Drawings

17-α-ACYL STEROIDS WHICH INHIBIT 5-α-REDUCTASE

CONTINUING DATA

This application is a 371 of PCT application PCT/US93/11235.

1. Field of the Invention

The present invention relates to novel substituted 17-α acyl steroidal 5α-reductase inhibiting compounds, pharmaceutical compositions containing these compounds and methods for using these compounds to inhibit steroid 5α-reductase. Also invented are novel processes useful in preparing these compounds.

2. Description of Related Art

The class of steroidal hormones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective control results in excessive androgen hormone production. For example, acne vulgaris, seborrhea, female hirsutism, male pattern baldness and prostatic hypertrophy are correlated with elevated androgen levels. Additionally, the reduction of androgen levels has been shown to have a therapeutic effect on prostate cancer.

Testosterone is the principal androgen secreted by the testes and is the primary androgenic steroid in the plasma of males. It now is known that 5-α-reduced androgens are the active hormones in some tissues such as the prostate and sebaceous gland. Circulating testosterone thus serves as a prohormone for dihydrotestosterone (DHT), its 5-α-reduced analogue, in these tissues but not in others such as muscle and testis. Steroid 5-α-reductase is a Nicotinamide Adenine dinucleotide Phosphate (NADPH) dependent enzyme that converts testosterone to DHT. The importance of this enzyme in male development was dramatically underscored by the discovery of a genetic steroid 5-α-reductase deficiency in male pseudohermaphrodites. Imperato-McGinley, J., et al., (1979), *J. Steroid Biochem.* 11:637–648.

Recognition of the importance of elevated DHT levels in various disease states has stimulated many efforts to synthesize inhibitors of this enzyme. Among the most potent inhibitors identified to date are 17β-acyl steroidal derivatives.

A number of substituted 17β-acyl steroidal 5α-reductase inhibiting compounds are know in the art. For example, U.S. Pat. No. 4,760,071 describes a class of substituted 17β-acyl-4-aza-steroidal 5α-reductase inhibiting compounds.

U.S. Pat. No. 4,970,204 describes a class of substituted 17β-acyl-3-nitro steroidal 5α-reductase inhibiting compounds.

U.S. Pat. No. 5,017,568 describes a class of substituted 17β-acyl-3-carboxylic acid steroidal 5α-reductase inhibiting compounds.

U.S. Pat. No 4,954,446 describes a class of substituted 17β-acyl A ring aryl 3-carboxylic acid steroidal 5α-reductase inhibiting compounds.

U.S. Pat. No. 4,970,205 describes a class of substituted 17β-acyl A ring aryl 3-sulfonic acid steroidal 5α reductase inhibiting compounds.

U.S. Pat. No. 4,910,226 describes a class of substituted 17β-acyl A nor 2-carboxylic acid steroidal 5α reductase inhibiting compounds.

U.S. Pat. No. 4,937,237 describes a class of substituted 17β-acyl A ring aryl 3-phosphonic acid steroidal 5α reductase inhibiting compounds.

U.S. Pat. No. 4,882,319 describes a class of substituted 17β-acyl A ring aryl 3-phosphinic acid steroidal 5α reductase inhibiting compounds.

U.S. Pat. No. 5,026,882 describes a class of substituted 17α-acyl 3-phosphinic acid steroidal 5α reductase inhibiting compounds.

U.S. Pat. No. 4,946,834 describes a class of substituted 17β-acyl 3-phosphonic acid steroidal 5α reductase inhibiting compounds.

WO 91/19732 describes a class of substituted 17β-acyl 3-acetic acid steroidal 5α reductase inhibiting compounds.

U.S. Pat. No. 5,100,917 describes substituted 175β-acyl A nor 3-carboxylic acid steroidal 5α reductase inhibiting compounds.

WO 91/267098-36 describes a class of substituted 175β-acyl-4-aza 5α reductase inhibiting compounds.

However, none of the cited references disclose or suggest the α-epimer of substituted 17β-acyl steroidal 5α reductase inhibiting compounds or teaches or suggest that said α-epimers would have utility as highly potent inhibitors of steroid 5α-reductase.

SUMMARY OF THE INVENTION

This invention relates to compounds which are substituted 17α-acyl 5α-reductase inhibiting steroidal compounds and methods of using these compounds to inhibit steroid 5α-reductase. In a further aspect of the invention there is provided novel processes useful in preparing the presently invented 5α-reductase inhibiting compounds. Included in the present invention are pharmaceutical compositions comprising a pharmaceutical carrier and compounds useful in the methods of the invention.

DETAILED DESCRIPTION OF THE INVENTION

By the term "substituted 17β-acyl" as used herein is meant a substituent at $C_{17}$ of a steroidal 5α-reductase inhibiting compound of the formula (I)

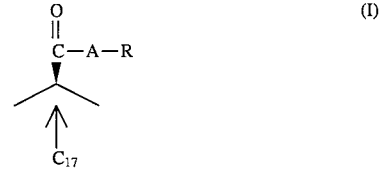

wherein A is absent or present as $C_{1-12}$ linear or branched alkylidene and examples of the term "R" as used herein includes but are not limited to;

i) hydrogen, hydroxyl, $C_{1-8}$alkyl, hydroxy$C_{1-8}$alkyl, $C_{1-8}$alkoxy, $NR^1R^2$ where $R^1$ and $R^2$ are each independently selected from hydrogen, $C_{1-8}$alkyl, $C_{3-6}$cycloalkyl or phenyl; or ii) substituted alkyl, cycloalkyl or aryl where a) substituted alkyl is linear or branched $C_1$–$C_{12}$ substituted with one or more substituents selected from the group consisting of: aryl, acyloxy, amino, N-acylamino, oxo, carboxyalkyl, halogen and protected —OH;

b) cycloalkyl is nonaromatic, unsaturated or saturated, cyclic or polycyclic $C_3$–$C_{12}$, optionally containing one or more heteroatoms, and optionally substituted with one or more substituents selected from the group consisting of: aryl, hydroxyalkyl, alkyl, alkoxy, acyloxy, amino, N-acylamino, oxo, carboxyalkyl, halogen and protected —OH; and c) aryl is cyclic or polycyclic aromatic $C_3$–$C_{12}$, optionally containing one or more heteroatoms, provided that when C is 3 the aromatic ring contains at least two heteroatoms and when C is 4 the aromatic ring contains at least one hetero atom, and optionally substituted with one or more substituents selected from the group consisting of: alkyl, $C_6$–$C_{12}$ aryl, hydroxyalkyl, alkoxy, acyloxy, amino, N-acylamino, nitro, cyano, halogen, carboxyalkyl, —$S(O)_nR^5$, protected —OH, where n is 0–2, and $R^5$ is hydrogen, alkyl, substituted alkyl, cycloalkyl or $C_6$–$C_{12}$ aryl.

Preferably R is as illustrated above.

Preferably R is $NR^1R^2$ where $R^1$ and $R^2$ are each independently selected from hydrogen and a substitutent selected from the group consisting of; hydrogen, $C_{1-8}$alkyl, $C_{3-6}$cycloalkyl and phenyl.

The compounds of this invention which inhibit 5α-reductase are the 17α-epimer derivatives of substituted 17β-acyl steroidal 5α-reductase inhibiting compounds and pharmaceutically acceptable salts, hydrates, solvates and esters thereof.

Persons skilled in the art can readily determine if a substituted 17β-acyl steroidal compound is asteroid 5α-reductase inhibitor by known methods. The α-epimer of all such compounds are included within the scope of this invention.

Substituted 17β-acyl steroidal 5α reductase inhibiting compounds are considered herein as starting material used to prepare the presently invented 17α-acyl steroidal 5α reductase inhibiting compounds.

By the term "α-epimer" as used herein is meant that the 17β-acyl substituent of the steroidal 5α reductase inhibitors disclosed herein as starting material is transformed to the α-position.

Preferred compounds of the invention and compounds used in the invented pharmaceutical compositions and the invented methods include:

17α-(N-t-butylcarboxamide)-5-5-androst-1-ene-4-aza-3-one,
17α-(N,N-diisopropylcarboxamide)-3-nitro-5-α-androst-3-ene,
17α-(N-t-butylcarboxamide)-3-nitro-5-α-androst-3-ene,
17α-(N,N-diisopropylcarboxamide)-3-nitro-5-α-androst-2-ene,
17α-(N-t-butylcarboxamide)-androst-3,5-diene-3-carboxylic acid or a salt thereof,
17α-(N,N-diisopropylcarboxamide)-androst-3,5-diene-3-carboxylic acid or a salt thereof,
17α-(N,N-diisopropylcarboxamide)-estra-1,3,5(10)-triene-3-carboxylic acid or a salt thereof.
17α-(N-t-butylcarboxamide)-estra-1,3,5(10)-triene-3-carboxylic acid or a salt thereof,
17α-(N,N-diisopropylcarboxamide)-estra-1,3,5(10)-triene-3-sulfonic acid or a salt thereof,
20-α-(hydroxymethyl)-A-nor-5-α-pregn-1-ene-2-carboxylic acid or a salt thereof,
17α-(N-t-butylcarboxamide)-estra-1,3,5(10)-triene-3-sulfonic acid or a salt thereof,
17α-(N,N-diisopropylcarboxamide)-estra-1,3,5(10)-triene-3-phosphonic acid or a salt thereof,
17α-(N-t-butylcarboxamide)-estra-1,3,5(10)-triene-3-phosphonic acid or a salt thereof,
17α-(N,N-diisopropylcarboxamide)-estra-1,3,5(10)-triene-3-phosphinic acid or a salt thereof,
17α-(N-t-butylcarboxamide)-estra-1,3,5(10)-triene-3-phosphinic acid or a salt thereof,
17α-(N-t-butylcarboxamide)-androst-3,5-diene-3-phosphinic acid or a salt thereof,
17α-(N,N-diisopropylcarboxamide)-androst-3,5-diene-3-phosphinic acid or a salt thereof,
17α-(N-t-butylcarboxamide)-androst-3,5-diene-3-phosphonic acid or a salt thereof,
17α-(N,N-diisopropylcarboxamide)-androst-3,5-diene-3-phosphonic acid or a salt thereof,
(E)-17α-(N,N-diisopropylcarboxamide)-androst-4-ene-3-ylidene-acetic acid,
17α-(N,N-diisopropylcarboxamide)-androst-3,5-diene-3-acetic acid,
(Z)-17α-(N,N-diisopropylcarboxamide)-androst-4-ene-3-ylidene-acetic acid,
17α-(N,N-diisopropylcarboxamide)-5α-androst-2-ene-3-acetic acid,
(Z)-17α-(N,N-diisopropylcarboxamide)-5α-androst-3-ylidene-acetic acid,
17α-(N,N-diisopropylcarboxamide)-5α-androst-3-ene-3-acetic acid,
17α-(N-t-butylcarboxamide)-5α-androst-2-ene-3-acetic acid, and
17α-(N-t-butylcarboxamide)-A nor-androst-3-ene-3-carboxylic acid.

Particularly preferred among the above listed compounds are:

17α-(N-t-butylcarboxamide)-androst-3,5-diene-3-carboxylic acid or a salt thereof,
17α-(N-t-butylcarboxamide)-estra-1,3,5(10)-triene-3-carboxylic acid or a salt thereof, and
17α-(N-t-butylcarboxamide)-5-α-androst-1-ene-4-aza-3-one.

The corresponding 17β-epimers of the above preferred compounds are known and have been shown to be potent inhibitors of steroid 5α reductase.

By the term "protected hydroxy" or "protected-OH" as used herein, is meant the alcoholic or carboxylic-OH groups which can be protected by conventional blocking groups in the art as described in "Protective Groups In Organic Synthesis" by Theodora W. Greene, Wiley-Interscience, 1981, New York. Preferred are the triorganosilyl groups, e.g. t-butyldimethylsilyl, phenyldimethylsilyl, diphenylmethylsilyl, and the like. As used herein $C_x$–$C_y$ is meant a moiety having from x to y carbons.

By the term "aryl" as used herein, unless otherwise defined, is meant cyclic or polycyclic aromatic $C_3$–$C_{12}$, optionally containing one or more heteroatoms, provided that when C is 3 the aromatic ring contains at least two heteroatoms and when C is 4 the aromatic ring contains at least one hetero atom, and optionally substituted with one or more substituents selected from the group consisting of: alkyl, $C_6$–$C_{12}$ aryl, hydroxyalkyl, alkoxy, acyloxy, amino, N-acylamino, nitro, cyano, halogen, carboxyalkyl, —$S(O)_n{}^{R5}$, protected —OH, where n is 0–2, and $R^5$ is hydrogen, alkyl, substituted alkyl, cycloalkyl or $C_6$–$C_{12}$ aryl.

Examples of aryl and substituted aryl as used herein include: phenyl, naphthyl, biphenyl, 4-fluorophenyl, 4-hydroxy-phenyl, 3,4-dihydroxyphenyl, 3,5-dimethyl-4-hydroxyphenyl, 4-methoxyphenyl and 4-carboxymethylphenyl.

By the term "$C_6$–$C_{12}$ aryl" as used herein, is meant substituted or unsubstituted phenyl, naphthyl or biphenyl.

By the term "alkoxy" as used herein is meant —Oalkyl where alkyl is as described herein including —$OCH_3$ and —$OC(CH_3)_2CH_3$.

Examples of cycloalkyl and substituted cycloalkyl as used herein include: cyclohexyl, 4-hydroxycyclohexyl, ethylcyclohexyl, propyl 4-methoxycyclohexyl, 4-methoxycyclohexyl, 4-carboxycyclohexyl and cyclopentyl.

By the term "acyloxy" as used herein is meant —OC(O) alkyl where alkyl is as described herein. Examples of acyloxy substituents as used herein include: —$OC(O)CH_3$, —$OC(O)CH(CH_3)_2$ and —$OC(O)(CH_2)_3CH_3$.

By the term "N-acylamino" as used herein is meant —N(H)C(O) alkyl, where alkyl is as described herein. Examples of N-acylamino as used herein include: —N(H)C(O)$CH_3$, —N(H)C(O)$CH(CH_3)_2$ and —N(H)C(O)$(CH_2)_3CH_3$.

By the term "heteroatom" as used herein is meant oxygen, nitrogen or sulfur.

By the term "halogen" as used herein is meant a substituent selected from bromide, iodide, chloride and fluoride.

By the term "alkyl" and "alkylidene" and derivatives thereof and in all carbon chains as used herein is meant a linear or branched monovalent or divalent carbon chain having $C_1$–$C_{12}$ carbons. Examples of alkyl as used herein included: —$CH_3$, —$CH_2$—$CH_3$, —$CH_2$—$CH_2$—$CH_3$, —$CH(CH_3)_2$, —$(CH_2)_3$, —$CH_3$, $CH_2$—$CH(CH_3)_2$, and —$CH(CH_3)$ —$CH_2$—$CH_3$. Examples of alkylidene as used herein include: —$CH_2$—, —$CH_2$—$CH_2$—, —$CH_2$—$CH_2$—$CH_2$—, —$CH(CH_3)CH_2$—, —$CH_2$—$CH_2$—$CH_2$, —$CH_2CH$ $(CH_3)$ $CH_2$—, —$CH(CH_3)CH_2$—$CH_2$—, and —$C(CH_3)_2$—$CH_2$—.

By the term "substituted" as used herein, unless otherwise defined, is meant that the subject chemical moiety has one or more substituents selected from the group consisting of: alkyl, aryl, hydroxyalkyl, alkoxy, acyloxy, amino, N-acyl amino, oxo, carboxyalkyl, halogen and protected —OH.

By the term "treating" and derivatives thereof as used herein, is meant prophylactic or therapeutic therapy.

The pharmaceutically active compounds of the present invention are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics for use as sustained release or prodrug formulations.

The term "α-receptor antagonist", as used herein, refers to a known class of alpha-andrenergic receptor antagonist compounds, such as described in Lafferty, et al. U.S. Pat. No. 4,963,547, which are utilized in treating vascular disorders such as diabetes, cardiovascular disease, benign prostatic hypertrophy and ocular hypertension.

Preferred alpha-andrenergic receptor antagonists for use in the compositions and methods of the invention include amsulosin, terazocin, doxazosin, alfuzosin, indoramin and prazosin.

By the term "amsulosin" as used herein is meant a compound of the formula.

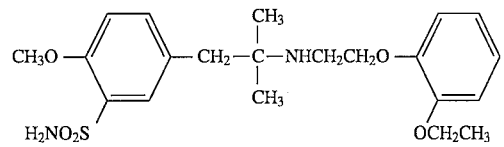

and salts, hydrates and solvates thereof.

Chemically, amsulosin is designated as (-)- (R)-5-[2-[[2-(O-ethoxyphenoxy)ethyl]amino]propyl]-2-methoxybenzenesulfonamide.

Amulosin is disclosed in U.S. Pat. No. 4,703,063 and claimed in U.S. Pat. No. 4,987,125 as being useful in treating lower urinary tract dysfunction.

By the term "terazocin" as used herein is meant a compound of the formula

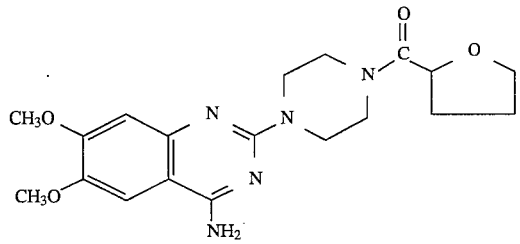

and salts, hydrates and solvates thereof.

Chemically, terazocin is designated as 1-(4-amino-6,7-dimethoxy-2 quinazolinyl)-4-[(tetrahydro-2-furoyl)carbonyl]piperazine. Terazocin is disclosed in U.S. Pat. No. 4,251,532.

By the term doxazosin as used herein is meant a compound of the formula

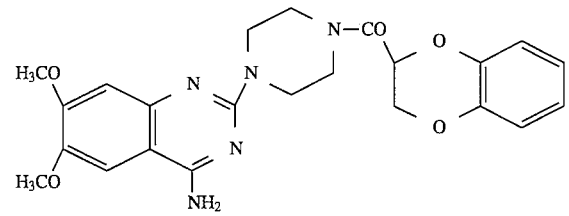

and salts, hydrates and solvates thereof.

Chemically "doxazosin" is designated as 1-(4-amino-6,7-dimethoxy-2-quinazolinyl)-4-[(2,3-dihydro-1,4-benzodioxin-2-yl)carbonyl]-piperazine.

Doxazosin is disclosed in U.S. Pat. No. 4,188,390.

By the term "alfuzosin" as used herein is meant a compound of the formula

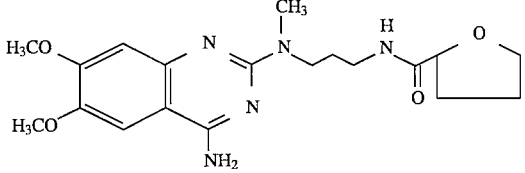

and salts, hydrates and solvates thereof.

Chemically alfuzosin is designated as N-[3-[(4-amino-6, 7-dimethoxy-2-quinazolinyl)methylamino]propyl]tetrahydro-2-furancarboxamide.

Alfuzosin is disclosed in U.S. Pat. No. 4,315,007.

By the term "indoramin" as used herein is meant a compound of the formula

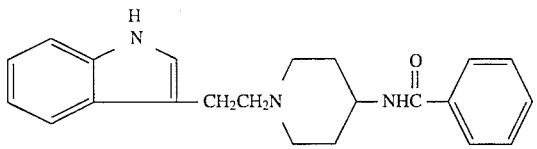

and salts, hydrates and solvates thereof.

Chemically indoramin as designated N-[[1-[2-(1H-indol-3-yl)ethyl]-4-piperidinyl]benzamine.

Indoramin is disclosed in U.S. Pat. No. 3,527,761.

By the term "prazosin" as used herein is meant a compound of the formula

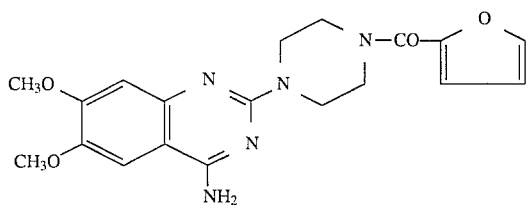

and salts, hydrates and solvates thereof.

Chemically prazosin is designated as 1-(4-amino-6,7-dimethoxy-2-quinazolinyl)-4-(2-furanylcarbonyl)-piperazine.

Prazosin is disclosed in U.S. Pat. No. 3,511,836.

Persons skilled in the art can readily determine if a compound other than one specifically referred to herein is a alpha-andrenergic receptor antagonist by utilizing the assay described in Lafferty I. Thus, all such compounds are included within the scope of the term "alpha-andrenergic receptor antagonist" as used herein.

By the term "minoxidil" as used herein is meant the compound of the formula:

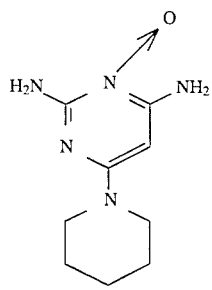

chemically minoxidil is designated as 2,4-pyrimidineadiamine, 6-(1-piperidinyl)-, 3-oxide. Minoxidil is the active ingredient in Rogaine® which is sold as topical solution for stimulating hair growth by the Upjohn Company, Kalamazoo, Mich.

As used herein, when a pharmaceutical composition contains a 5-α-reductase inhibitor, as described herein and a further active ingredient, said 5-α-reductase inhibitor can be co-administered with said further active ingredient.

By the term "co-administering" and derivative thereof as used herein is meant either simultaneous administration or any manner of consecutive administration of a 5-α-reductase inhibiting compound, as described herein, and a further active ingredient, such as other compounds known to treat the disease states of acne vulgaris, seborrhea, female hirsutism, male pattern baldness, benign prostate hypertrophy or human prostatic adenocarcinoma. Preferably, if the administration is not simultaneous, the two compounds are administered in a close time proximity to each other. Furthermore, it does not matter if the compounds are both administered in the same dosage form, e.g. one compound may be administered by injection and the other compound may be administered orally.

The substituted 17β-acyl steroidal 5α-reductase inhibitors which are considered starting material herein will be known and shown to be potent inhibitors of steroid 5-α-reductase.

Under standard synthetic conditions the steroidal 17β-acyl substituent, as described herein, is formed.

The presently invented substituted 17α-acyl steroidal 5α-reductase inhibiting compounds are prepared by epimerization of the corresponding substituted 17'-acyl steroidal 5'-reductase inhibiting compound as described in the general method below.

General Method A

To a stirred solution of a substituted 17β-acyl steroidal 5α-reductase inhibiting compound in an appropriate solvent, preferably ethylene glycol or dimethyl sulfoxide, is added a base such as a hydroxide or alkoxide base, preferably sodium hydroxide, potassium hydroxide or sodium methoxide, at increased temperatures preferably at reflux temperatures to yield the corresponding α epimer, after isolation and work up.

In determining the appropriate solvent for conducting the epimerization, dimethyl sulfoxide or other non-reactive high boiling solvents are preferred when the starting 17β-acyl 5α-reductase inhibiting steroidal compound contains reactive substituents or reactive unsaturated bonds that are, for example, subject to nucleophilic attack and ethylene Glycol, or other reactive high boiling solvents can be used when the reactivity of the substituents or any unsaturated bonds of the starting 17β-acyl 5α-reductase inhibiting steroidal compound is not a consideration.

Also within the scope of the present invention is the ketone reduction product of the presently invented 17α-acyl steroidal compounds.

By the term "ketone reduction product" as used herein is meant the corresponding secondary alcohol of the 17α-acyl substituents of the presently invented compounds said corresponding secondary alcohol having the structure

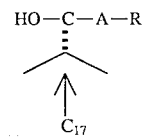

in which A and R are as defined above and pharmaceutically acceptable salts, hydrates, solvates and esters thereof.

These compounds can be made by conventional sodium borohydride reduction of the carbonyl attached to R without reducing other steroidal functional groups or degrees of unsaturation. If R is a phenyl which contains a carbonyl function, it can be selectively blocked and then regenerated after the borohydride reduction by conventional methods.

The borohydride reduction can be carried out in e.g. water or aqueous methanol, at a temperature of room temperature to 50° C. and the product then isolated and purified by conventional means. The compounds are also active as 5-alpha reductase inhibitors.

By the term "increased temperatures" as used herein and in the claims is meant above 100° C., preferably above 120° C., most preferably at reflux temperatures.

Pharmaceutically acceptable salts, hydrates solvates and esters of Formula (I) compounds are formed, where appropriate, by methods well known to those of skill in the art.

Because the presently invented pharmaceutically active compound inhibit steroid 5-α-reductase activity, they have therapeutic utility in treating diseases and conditions wherein decreases in DHT activity produces the desired therapeutic effect. Such diseases and conditions include acne vulgaris, seborrhea, female hirsutism, male pattern baldness, prostate diseases such as benign prostatic hypertrophy, and human prostatic adenocarcinoma.

In determining potency in inhibiting the human 5α-reductase enzyme, the following procedure was employed:
Preparation of membrane particulates used as source for steroid 5α-reductase isozyme 1.

Chinese hamster ovary (CHO) cells containing expressed, recombinant human steroid 5α-reductase isoenzyme 1 (Andersson, S., Berman, D. M., Jenkins, E. P., and Russell, D. W. (199) Nature 354 159–161) were homogenized in 20 mM potassium phosphate, pH 6.5, buffer containing 0.33M sucrose, 1 mM dithiothreitol, and 50 μM NADPH (buffer A) using a Dounce glass-to-glass hand homogenizer (Kontes Glass Co., Vineland, N.J.). Membrane particulates were isolated by centrifugation (100,000× g at 4° C. for 60 minutes) and resuspended in 20 mM potassium phosphate, pH 6.5, containing 20% glycerol, 1 mM dithiothreitol, and 50 μM NADPH (buffer B). The suspended particulate solution was stored at −80° C.

Preparation of prostatic membrane particulates used as source for steroid 5α-reductase isozyme 2.

Frozen human prostates were thawed and minced into small pieces (Brinkmann Polytron (Sybron Corp., Westbury, N.Y.). The solution was sonicated for 3 to 5 minutes with a Sonifier (Branson Sonic Power Co.) followed by hand homogenization in a Dounce hand homogenizer. Prostatic particles were obtained by differential centrifugation at 600 or 1000× g for 20 minutes and 140,000× g for 60 minutes at 4° C. The pellet obtained from the 140,000× g centrifugation was washed with 5 to 10 tissue volumes of the buffer described above and centrifuged at 140,000× g. The resulting pellet was suspended in buffer B and the particulate suspension was stored at −80° C.

Assay for enzymes activities and inhibitors potency.

A constant amount of [$^{14}$C] testosterone (50 to 55 mCi/mmol) in ethanol and varying amounts of potential inhibitor in ethanol were deposited in test tubes and concentrated to dryness in vacuo. To each tube was added buffer, 10 μL (isoenzyme 1) or 20 μL (isoenzyme 2) of 10 mM NADPH and an aliquot of asteroid 5α-reductase preparation to a final volume of 0.5 mL. Assays for human steroid 5α-reductase isoenzyme 1 were conducted with a sample of the recombinant protein expressed in CHO cells in 50 mM phosphate buffer, pH 7.5 while assays of isoenzyme 2 were conducted with a suspension of human prostatic particulates in 50 mM citrate buffer at pH 5.0.

After incubating the solution at 37° C. for 20 or 30 minutes the reaction was quenched by the addition of 4 mL ethyl acetate and 0.25 μmol each of testosterone, 5α-dihydrotestosterone, androstanediol, and androstanedione as carriers. The organic layer was removed to a second test tube and evaporated to dryness in a Speed Vac. The residue was dissolved in 40 μL chloroform, spotted on an individual lane of a 20×20 cm prechannelled silica gel TLC plate (Si 250F-PA, Baker Chemical) and developed twice with acetone:chloroform (1:9). The radiochemical content in the bands of the substrate and the products was determined with a BIOSCAN Imaging Scanner (Bioscan Inc., Washington, D.C.). The percent of recovered radiolabel converted to product was calculated, from which enzyme activity was determined. All incubations were conducted such that no more than 20% of the substrate (testosterone) was consumed.

The experimentally obtained data was computer fit to a linear function by plotting the reciprocal of the enzyme activity (1/velocity) against the variable inhibitor concentration; apparent inhibition constants ($K_{i,app}$) were determined by the Dixon analysis (Dixon, M. (1953).

The value for the inhibition constant (Ki) was calculated from known procedures (Levy, M. (1989), *Biochemistry*, 29:2815–2824).

All of the compounds within the scope of this invention are useful in inhibiting steroid 5-α-reductase in a mammal, including humans, in need thereof.

Compounds within the scope of this invention have been tested and have shown an activity of from 20–40 to 2300 Ki (nM) against isozyme 1 and an activity of from 2–6 to 26 Ki (nM) against isozyme 2. Particularly preferred among the compounds of the invention and the compounds used in the invented pharmaceutical compositions and invented methods are 17α-(N-t-butylcarboxamide)-androst-3,5-diene-3-carboxylic acid and 17α-(N-t-butylcarbonamide-estra-1,3, 5(10)-triene-3-carboxylic acid.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.1–1000 mg/kg of active compound, preferably 1–100 mg/kg. The selected dose is administered preferably to a human patient in need of steroid 5-α-reductase inhibition preferably from 1–6 times daily orally, or parenterally.

Preferred forms of parenteral administration include; topically, rectally, transdermally, by injection and continuously by infusion.

Oral dosage units for human administration preferably contain from 1 to 500 mg of active compound. Oral administration, which uses lower dosages is preferred. Parenteral administration, at high dosages, however, also can be used when safe and convenient for the patient.

The method of this invention of inhibiting steroid 5-α-reductase activity in mammals, including humans, comprises administering to a subject in need of such inhibition an effective steroid 5-α-reductase inhibiting amount of a pharmaceutically active compound of the present invention.

No unacceptable toxicological effects are expected when compounds of the invention are administered in accordance with the present invention.

In addition, the compounds of the present invention can be co-administered with further active ingredients, such as other compounds known to treat the disease states of acne vulgaris, seborrhea, female hirsutism, male pattern baldness, benign prostate hypertrophy or human prostatic adenocarcinoma. Particularly preferred is a combination of a 5-α-reductase inhibitor, as disclosed herein, and minoxidil for use in the treatment of male pattern baldness. Particularly preferred is a combination of a 5α-reductase inhibitor, as disclosed herein, and a α-receptor antagonist for use in the treatment of benign prostatic hypertrophy.

The following examples illustrate preparation of the compounds of this invention and pharmaceutical compositions containing these compounds. The examples are not intended to limit the scope of the invention as defined herein above and as claimed below.

EXAMPLE 1

Epimerization of 17β-(N-t-butylcarboxamide)-androst-3,5-diene-3-carboxylic acid in ethylene glycol

General Methods

Melting points were determined on a Thomas-Hoover capillary melting point apparatus and are uncorrected. Elemental analyses were done on a Perkin Elmer Model 240 CHN Elemental Analyzer; the results found are within acceptable limits (0.4%) of the theoretical values. Common reagent—grade chemicals were purchased from Aldrich Chemical Co. and were used as received.

Analytical HPLC analyses of samples were determined on an IBM LC/9533 ternary gradient liquid chromatograph equipped with an IBM LC/9523 variable wavelength detector coupled to an IBM LC/9000 computer system which serves as a recorder/integrator. The preparative chromatographic system consisted of a Varex Preparative Scale LC (PSLC-100) fitted with a LCD/Milton Roy SpectroMonitor 111 variable wavelength detector and a Health Strip Chart recorder Model SR 255-B. The following reversed phase HPLC systems were used: (a) analytical: injection volume 20 microliters; chromegabond MC18, 10 micron, 4.5 mm×25 cm column; 40% water, 30% acetonitrile, 25% methanol and 0.1% TFA mobile phase; flow at 1 mL/min; detection at 270 nm, (b) preparative: injection volume 5 mL; Chromegabond MC18, 10 micron, 22.2 mm×50 cm column.

The preparative mobile phase employed (A) consisted of: 40% water, 30% acetonitrile, 25% methanol and 0.1% TFA; flow at 40 mL/min; detection at 270 nm.

i) Procedure using sodium hydroxide

Into a 250 mL 3-neck round bottom flask was placed 4.0 g (0.01 mmoles) of 17β-(N-t-butylcarboxamide)-androst-3,5-diene-3-carboxylic acid and 5.0 g (0.125 mmoles) of sodium hydroxide. To the flask was added approximately 75 mL of ethylene glycol. The system was heated at reflux (~155° C.) and the reaction monitored by HPLC; reaction composition and time of reaction are tabulated below.

| | Percent (%) Composition | |
|---|---|---|
| Time (hr) | 17β-(N-t-butylcarboxamide)-androst 3,5-diene-3-carboxylic acid | Major Reaction Product |
| 1.0 | 92.72 | 7.28 |
| 2.0 | 83.31 | 16.69 |
| 20.0 | 70.00 | 30.00 |
| 21.0 | 69.09 | 30.91 |
| 24.0 | 70.71 | 29.29 |

At the end of 24 hrs., the straw coloured solution was cooled to room temperature and transferred into a beaker containing approximately 750 mL of deionized water; the water was stirred as the reaction mixture was added. After complete mixing, the solution was acidified to pH ~2.0 with dilute (6N) hydrochloric acid. At this point the compounds precipitated from the aqueous system, and were extracted with methylene chloride (3×100 mL).

The combined organic extracts was washed with water (2×100 mL) dried over anhydrous magnesium sulfate and then evaporated to dryness. Acetonitrile was added to the residue and the compounds crystallized. The mixture was filtered, the residue washed with cold acetonitrile and dried in a vacuum oven at 60° C. for 16 hrs. Yield ~2.5 g of reaction product.

To the 2.5 g of reaction product was added ~150 mL of the preparative scale mobile phase (A). Five mL aliquots (about 30) of the solution were applied to the preparative column and elution of the components was achieved with the preparative mobile phase (A) at a flow of 40 mL/min and the eluate monitored with UV at 270 nm. Five main fractions were collected and each analyzed by the analytical method. The analytical chromatograms show that (a) factions 1 and 2 contain minor decomposition products which are more polar than 17β-(N-t-butylcarboxamide)androst-3,5-diene-3-carboxylic acid, (b) one major reaction product was the predominating species in fraction 3, (c) fraction 4 was essentially a mixture of the major reaction product and unreacted 17β-(N-t-butylcarboxamide)androst-3,5-diene-3-carboxylic acid and (d) unreacted 17β-(N-t-butylcarboxamide) androst-3,5-diene-3-carboxylic acid which was the major component in fraction 5.

All of the fractions designated Fraction 3, were combined and concentrated to approximately 500 mL; as the volume of the solution was reduced, a solid material precipitated. The solid was isolated by filtering, washing the residue with a methanol/water mixture (50:50) and drying in a vacuum oven at room temperature for 18 hrs. Yield ~850 mg of product; purity, 95% (HPLC) by area normalization.

A methanolic solution of said product was diluted to approximately 50 mL, and water added until the solution was cloudy (~25 mL). The cloudy solution was allowed to sit at room temperature overnight during which time the sample crystallized. This mixture was filtered and the residue washed with water and dried in a vacuum oven at 60° C. for 16 hrs. Yield ~520 mg of the major reaction product; purity, 98% (HPLC) area normalization; m.pt. 240°–242° C.

Elemental analysis, NMR and Nuclear Overhauser effect (NOe) data confirmed that the major reaction product is the 17α epimer of 17β-(N-t-butylcarboxamide)-androst-3,5-diene-3-carboxylic acid, i.e. 17α-(N-t-butylcarboxamide)-androst-3,5-diene-3-carboxylic acid.

Anal. Calcd for $C_{25}H_{37}NO_3$: C, 75.15; H, 9.33; N, 3.51. Found: C, 75.19; H, 9.18; N, 3.40.

The assignment of the α-epimer configuration was based on observation of a strong Nuclear Overhauser effect (NOe) at the 17-methine proton on irradiation of the 18-methyl signal (the NMR signals of both the 17-methine proton and the 18-methyl group having previously been unambiguously identified from analysis of homonuclear and $^{13}C/^{1}H$ 2-D correlation data). The key observation is a strong enhancement elicited at H17 on irradiation of $CH_3$–18.

ii) Procedure using potassium hydroxide

Having identified by HPLC profile the α epimer of 17β-(N-t-butylcarboxamide)-androst-3,5-diene-3-carboxylic acid in procedure (i) above, the reaction was repeated using potassium hydroxide and monitored by an analytical HPLC, according to the general methods of Example 1, to determine the ratio of starting material to product.

Into a 250 mL 3-neck round bottom flask was placed 4.0 g (0.01 moles) of 17β-(N-t-butylcarboxamide)-androst-3,5-diene-3-carboxylic acid and 8.0 g (0.143 mmoles) of potassium hydroxide. To the flask was added approximately 100 mL of ethylene glycol, and the system heated at reflux (~155° C.). The reaction was monitored by HPLC; reaction composition and time of reaction are tabulated below.

| Time (hr) | Area % (HPLC) Composition of Reaction Mixture | |
|---|---|---|
| | 17b-(N-t-butylcarboxamide)-androst-3,5-diene-3-carboxylic acid | 17a-(N-t-butylcarboxamide)-androst-3,5-diene-3-carboxylic acid |
| 2.0 | 88.07 | 10.65 |
| 4.0 | 80.63 | 17.05 |
| 72.0 | 61.10 | 29.31 |
| 96.0 | 58.53 | 27.33 |
| 120.0 | 51.53 | 23.19 |
| 144.0 | 53.99 | 24.11 |
| 168.0 | 52.28 | 22.81 |

As shown in the tabulated data above, the maximum α epimer concentration occurred at about 72 hours of reaction time.

Isolation of the major reaction product (i.e. 17α-(N-t-butylcarboxamide)-androst-3,5-diene-3-carboxylic acid) is performed as in Example 1 procedure (i).

EXAMPLE 2

Epimerization of 17β-(N-t-butylcarboxamide)-estra-1,3,5(10)-triene-3-carboxylic acid in ethylene glycol General Methods Melting points were determined on a Thomas-Hoover capillary melting point apparatus and are uncorrected. Elemental analyses were done on a Perkin Elmer Model 240 CHN elemental Analyzer; the results found are within acceptable limits (0.4%) of the theoretical values. Common reagent—grade chemicals were purchased from Aldrich Chemical Co. and were used as received.

Analytical HPLC analyses of samples were determined on an IBM LC/9533 ternary gradient liquid chromatograph equipped with an IBM LC/9523 variable wavelength detector coupled to an IBM LC/9000 computer system which serves as a recorder/integrator. The preparative chromatographic system consisted of a Varex Preparative Scale LC (PSLC-100) fitted with a LDC/Milton Roy SpectroMonitor 111 variable wavelength detector and a Health Strip Chart recorder Model SR 255-B. The following reversed phase HPLC systems were used: (a) analytical: injection volume 20 mmicroliters; Chromegabond MC18, 10 micron, 4.5 mm×25 cm column; 55% water containing 10% methanol, 45% acetonitrile and 0.1% TFA mobile phase; flow at 1 mL/min; detection at 254 nm (b) preparative injection volume 5 mL; Chromegabond MC18, 10 micron, 22.2 mm×50 cm column. One preparative mobile phase was employed; 52% water, 35% acetonitrile, 13% methanol and 0.1% TFA, flow at 42 mL/min; detection at 254 nm.

Into a 250 mL 3-neck round bottom flask was placed 8.0 g (0.02 mmoles) of 17β-(N-t-butylcarboxamide)-estra-1,3, 5-(10)-triene-3-carboxylic acid and 10.0 g (0.250 mmoles) of sodium hydroxide. To the flask was added approximately 150 mL of ethylene glycol.

The system was heated at reflux (~155° C.) and the reaction monitored by HPLC; reaction composition and time of reaction are tabulated below.

| Time (hr) | Percent (%) Composition | |
|---|---|---|
| | 17b-(N-t-butylcarboxamide)-estra-1,3,5(10)-triene-3-carboxylic acid | Major Reaction Product |
| 1.0 | 83.50 | 14.80 |
| 19.0 | 71.50 | 28.52 |
| 24.0 | 70.68 | 27.94 |

At the end of 24 hrs, 100 mL of the straw coloured solution was cooled to room temperature and transferred into a beaker containing approximately 750 mL of deionized water; the water was stirred as the reaction mixture was added. After this point the compounds precipitated from the aqueous system, and were extracted with methylene chloride (3×100 mL). The combined organic extracts was washed with water (2×100 mL) dried over anhydrous magnesium sulfate and then evaporated to dryness. Acetonitrile was added to the residue and the compounds crystallized. The mixture was filtered, the residue washed with cold acetonitrile and dried in a vacuum oven at 60° C. for 16 hrs. Yield ~6.0 g of reaction product (I).

To the 6.0 g of reaction product (I) was added ~160 mL of the preparative scale mobile phase. Four mL aliquots (about 40) of the solution were applied to the preparative column and elution of the components was achieved with the preparative mobile phase 52% water, 35% acetonitrile, 14% methanol and 0.1% TFA, flow at 42 mL/min; detection at 254 nm.

Three main fractions were collected and each analyzed by the analytical method. The analytical chromatograms show that fractions 1 contained mainly the major reaction product (b) fraction 2 was essentially a mixture of the major reaction product and unreacted and (c) unreacted which was the major component in fraction 3.

All of the fractions designated Fraction 1, were combined and concentrated to approximately 1000 mL. The volume was divided and lyophylized. A methanolic solution of the residue from each flask was diluted to approximately 50 mL, and water added until the solution was cloudy (~25 mL). Each cloudy solution was allowed to sit at room temperature overnight during which time the sample crystallized. The mixtures were filtered and the residues washed with water and dried in a vacuum oven at 60° C. for 16 hours Yields ~700 mg of the major reaction product; purity 98.8% (by area normalization) m.pt. 176°–180° C. and ~350 mg of the major reaction product; purity 98% (by area normalization) m.pt. 177°–180° C.

Elemental analysis, NMR and the observation of the uniform differences in $^{13}C$ shifts between the α and β epimers of the steroidal diene in experiment I and the starting β-epimer and the major reaction product of experiment II confirmed that the major reaction product is the 17-α epimer of 17β-(N-t-butylcarboxamide)-estra-1,3,5-triene-3-carboxylic acid, i.e. 17α-(N-t-butylcarboxamide)-androst-3,5-diene-3-carboxylic acid.

Anal. Calcd for $C_{24}H_{33}NO_3O$: C, 71.79; H, 8.79; N, 3.49 Found: C, 71.62; H, 8.80; N, 3.62

EXAMPLE 3

Epimerization of 17β-(N-t-butylcarboxamide)-androst-3,5-diene-3-carboxylic acid in dimethyl sulfoxide

Procedure

Having identified by HPLC profile the α epimer of 17β-(N-t-butylcarboxamide)-androst-3,5-diene-3-carboxylic acid in Example 1 procedure (i) above, the reaction was repeated using sodium hydroxide in dimethyl sulfoxide and monitored by analytical HPLC according to the general methods of Example 1 to determine the ration of starting material to product.

Into a 250 mL 3-neck round bottom flask were placed 4.0 g (0.01 mmoles) 17β-(N-t-butylcarboxamide)-androst-3,5-diene-3-carboxylic acid and 5.0 g (0.125 mmoles) of sodium hydroxide. To the flask was added 75 mL of dimethyl sulfoxide. The system was heated at reflux (~155° C.) and the reaction monitored by HPLC; reaction composition and time of reaction are tabulated below.

| | Percent (%) Composition | |
|---|---|---|
| Time (hr) | 17b-(N-t-butylcarboxamide)-androst-3,5-diene-3-carboxylic acid | 17a-(N-t-butylcarboxamide)-androst-3,5-diene-3-carboxylic acid |
| 1.0 | 88.58 | 11.42 |
| 2.0 | 68.14 | 31.80 |
| 3.0 | 63.00 | 33.00 |
| 4.0 | 64.00 | 35.00 |

As shown in the tabulated data above, the maximum α-epimer concentration occurred at about 4 hours of reaction time.

Isolation of Reaction Product

Reaction products were isolated by preparative HPLC using a Chromegabond MC18, 10 micron 22.2 mm×50 cm column and a mobile phase which comprise 40% water, 30% acetonitrile, 25% methanol and 0.1% TFA; detection was at 270 nm.

Into the reaction product was added ~200 mL of the preparative scale mobile phase 10 mL aliquots (about 25) of the solution were applied to the preparative column and elution of the components was achieved with the preparative mobile phase 40% water, 30% acetonitrile, 25% methanol and 0.1% TFA at 40 mL/min and the eluate monitored with UV at 270 nm. The chromatographic system consisted of a Varex Preparative Scale LC Model PSLC 100 (MC18, 10 micron 22.2 mm×50 cm column) with a LCD/Milton Roy Spectro Monitor 111, a variable wavelength detector and a Heath Strip chart recorder Model SR 255-B.

Three main fractions were collected and each analyzed by the analytical method. The analytical chromatograms show that fraction 1 was essentially the alpha epimer of 17β-(N,t-butylcarboxamide)-androst-3,5-diene-3-carboxylic acid, fraction 2 was a mixture of alpha and beta epimers of 17β-(N,t-butylcarboxamide)-androst-3,5-diene-3-carboxylic acid and fraction 3 was essentially 17β-(N,t-butylcarboxamide)-androst-3,5-diene-3-carboxylic acid.

All fractions designated fraction 1 were combined into a 4000 mL flask and the! volume of the solution reduced, a solid material precipitated. The solid was isolated by filtering, washing the residue with a methanol/water mixture 50:50 and drying in a vacuum oven at room temperature for 20 hours yield ~600 mg purity: 98.32% (HPLC).

EXAMPLE 4

Epimerization of 17β-(N-t-butylcarboxamide)-estra-1,3,5(10)-triene-3-carboxylic acid in Dimethyl Sulfoxide

Procedure

Having identified by HPLC profile the α epimer of 17β-(N-t-butylcarboxamide)-estra-1,3,5 (10)-triene-3-carboxylic acid in Example 2 above, the reaction was repeated using sodium hydroxide in dimethyl sulfoxide and monitored by analytical HPLC: according to the general methods of Example 2 to determine the ration of starting material to product.

Into a 250 mL 3-neck round bottom flask were placed 4.0 g of 17β-(N,t-butylcarboxamide)-estra-1,3,5(10)-triene-3-carboxylic acid and 5.0 g of sodium hydroxide. To the flask was added 75 mL of dimethyl sulfoxide. The system was heated at reflux (~155° C.) and the reaction monitored by HPLC; reaction composition and time of reaction are tabulated below.

| | Percent (%) Composition | |
|---|---|---|
| Time (hr) | 17β-(N-t-butylcarboxamide)-estra-1,3,5(10)-triene-3-carboxylic acid | 17α-(N-t-butylcarboxamide) estra-1,3,5(10)-triene-3-carboxylic acid |
| 1.0 | 75.88 | 24.12 |
| 2.0 | 73.57 | 26.43 |
| 3.0 | 66.87 | 34.13 |
| 4.0 | 65.06 | 34.93 |

As shown in the tabulated data above, the maximum α epimer concentration occurred at about 4 hours of reaction time.

Isolation of Reaction Product

Reaction products were isolated by preparative HPLC using a Detector, An Autosampler (Hewlett-Packard HP 1050 Series) plus a Pump (Beckman 126 System Gold) and a mobile phase which comprise 55% water, 45% acetonitrile, and 0.1% TFA; detection was at 254 nm.

Into the reaction product was added ~150 mL of the preparative scale mobile phase 10 mL aliquots (about 20) of the solution were applied to the preparative column and elution of the components was achieved with the preparative mobile phase 52% water, 35% acetonitrile, 13% methanol and 0.1% TFA at 40 mL/min and the eluate monitored with UV 254 nm. The chromatographic system consisted of a Varex Prep Scale LC Model PSLC 100 (MC18, 10 micron 22.2 mm×50 cm column) with a LCD/Milton Roy Spectro Monitor 111 variable wavelength detector and a Heat Strip Chart recorder Model SR 255-B.

Three main fractions were collected and each analyzed by the analytical method. The analytical chromatograms show that fraction 1 was essentially the alpha epimer of 17β-(N-t-butylcarboxamide)-estra-1,3,5(10)-triene-3-carboxylic acid, fraction 2 was a mixture of the alpha and the beta epimers of 17β-(N-t-butylcarboxamide)-estra-1,3,5(10)-triene-3-carboxylic acid and fraction 3 was essentially 17β-(N-t-butylcarboxamide)-estra-1,3,5(10)-triene-3-carboxylic acid.

All fractions designated fraction 1 were combined into a 2000 mL flask and the volume of the solution reduced causing a solid material to precipitate. The solid was isolated by filtering, washing the residue with a methanol/water mixture 50:50 and drying in the vacuum oven at room temperature for 20 hours; yield ~500 mg of the α epimer.

EXAMPLE 5

An oral dosage form for administering the α epimer of substituted 17β-acyl steroidal 5α-reductase inhibiting compounds is produced by screening, mixing, and filling into hard gelatin capsules the ingredients in the proportions shown in Table 1, below.

TABLE 1

| Ingredients | Amounts |
| --- | --- |
| 17α-(N-t-butylcarboxamide)-estra-1,3,5(10)-triene-3-carboxylic acid | 50 mg |
| magnesium stearate | 5 mg |
| lactose | 75 mg |

EXAMPLE 6

The sucrose, calcium sulfate dihydrate and an α epimer of substituted 17β-acyl steroidal 5α-reductase inhibiting compound shown in Table II below, are mixed and granulated in the proportions shown with a 10% gelatin solution. The wet granules are screened, dried, mixed with the starch, talc and stearic acid, screened and compressed into a tablet.

TABLE II

| Ingredients | Amounts |
| --- | --- |
| 17α-(N-t-butylcarboxamide)-androst-3,5-diene-3-carboxylic acid | 100 mg |
| calcium sulfate dihydrate | 150 mg |
| sucrose | 20 mg |
| starch | 10 mg |
| talc | 5 mg |
| stearic acid | 3 mg |

EXAMPLE 7

17α-(N-t-butylcarboxamide)-estra-1,3,5(10)-triene-3-carboxylic acid, 75 mg, is dispersed in 25 ml of normal saline to prepare an injectable preparation.

While the preferred embodiments of the invention are illustrated by the above, it is to be understood that the invention is not limited to the precise instructions herein disclosed and that the right to all modifications coming within the scope of the following claims is reserved.

What is claimed is:

1. The α-epimer of 17β-acyl 5α-reductase inhibiting steroidal compounds.

2. A compound of claim 1 in which the C17 substituent is of the formula

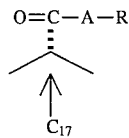

wherein A is absent or present as $C_{1-12}$ linear or branched alkylidene; and R is i). hydrogen, hydroxyl, $C_{1-8}$alkyl, hydroxy$C_{1-8}$alkyl, $C_{1-8}$alkoxy, $NR^1R^2$ where $R^1$ and $R^2$ are each independently selected from hydrogen, $C_{1-8}$alkyl, $C_{3-6}$cycloalkyl or phenyl; or ii). substituted alkyl, cycloalkyl or aryl where a) substituted alkyl is linear or branched $C_1$–$C_{12}$ substituted with one or more substituents selected from the group consisting of: aryl, acyloxy, amino, N-acylamino, oxo, carboxyalkyl, halogen and protected —OH;

b) cycloalkyl is nonaromatic, unsaturated or saturated, cyclic or polycyclic $C_3$–$C_{12}$, optionally containing one or more heteroatoms, and optionally substituted with one or more substituents selected from the group consisting of: aryl, hydroxyalkyl, alkyl, alkoxy, acyloxy, amino, N-acylamino, oxo, carboxyalkyl, halogen and protected —OH; and c) aryl is cyclic or polycyclic aromatic $C_3$–$C_{12}$, optionally containing one or more heteroatoms, provided that when C is 3 the aromatic ring contains at least two heteroatoms and when C is 4 the aromatic ring contains at least one hetero atom, and optionally substituted with one or more substituents selected from the group consisting of: alkyl, $C_6$–$C_{12}$ aryl, hydroxyalkyl, alkoxy, acyloxy, amino, N-acylamino, nitro, cyano, halogen, carboxyalkyl, $—S(O)_nR^5$, protected —OH, where n is 0–2, and $R^5$ is hydrogen, alkyl, substituted alkyl, cycloalkyl or $C_6$–$C_{12}$ aryl and pharmaceutically acceptable salts, hydrates, solvates and esters thereof.

3. A compound of claim 2 in which R is $NR^1R^2$ where $R^1$ and $R^2$ are each independently selected from hydrogen and a substituent selected from the group consisting of; hydrogen, $C_1$–$C_8$alkyl, $C_{3-6}$cycloalkyl and phenyl.

4. A compound of claim 2 which is:

17α-(N-t-butylcarboxamide)-5-α-androst-1-ene-4-aza-3-one,

17α-(N,N-diisopropylcarboxamide)-3-nitro-5-α-androst-3-ene,

17α-(N-t-butylcarboxamide)-3-nitro-5-α-androst-3-ene,

17α-(N,N-diisopropylcarboxamide)-3-nitro-5-α-androst-2-ene,

17α-(N-t-butylcarboxamide)-androst-3,5-diene-3-carboxylic acid or a salt thereof, 17α-(N,N-diisopropylcarboxamide)-androst-3,5-diene-3-carboxylic acid or a salt thereof, 17α-(N,N-diisopropylcarboxamide)-estra-1,3,5(10)-triene-3-carboxylic acid or a salt thereof, 17α-(N-t-butylcarboxamide)-estra-1,3,5(10)-triene-3-carboxylic acid or a salt thereof, 17α-(N,N-diisopropylcarboxamide)-estra-1,3,5(10)-triene-3-sulfonic acid or a salt thereof, 20-α-(hydroxymethyl)-A-nor-5-α-pregn-1-ene-2-carboxylic acid or a salt thereof, 17α-(N-t-butylcarboxamide)-estra-1,3,5(10)-triene-3-sulfonic acid or a salt thereof, 17α-(N,N-diisopropylcarboxamide)-estra-1,3,5(10)-triene-3-phosphonic acid or a salt thereof, 17α-(N-t-butylcarboxamide)-estra-1,3,5(10)-triene-3-phosphonic acid or a salt thereof, 17α-(N,N-diisopropylcarboxamide)-estra-1,3,5(10-triene-3-phosphinic acid or a salt thereof,
17α-(N-t-butylcarboxamide)-estra-1,3,5(10)-triene-3-phosphinic acid or a salt thereof,
17α-(N-t-butylcarboxamide)-androst-3,5-diene-3-phosphinic acid or a salt thereof,
17α-(N,N-diisopropylcarboxamide)-androst-3,5-diene-3-phosphinic acid or a salt thereof,
17α-(N-t-butylcarboxamide)-androst-3,5-diene-3-phosphonic acid or a salt thereof,
17α-(N,N-diisopropylcarboxamide)-androst-3,5-diene-3-phosphonic acid or a salt thereof,
(E)-17α-(N,N-diisopropylcarboxamide)-androst-4-ene-3-ylidene-acetic acid,
17α-(N,N-diisopropylcarboxamide)-androst-3,5-diene-3-acetic acid,
(Z)-17α-(N,N-diisopropylcarboxamide)-androst-4-ene-3-ylidene-acetic acid,
17α-(N,N-diisopropylcarboxamide)-5α-androst-2-ene-3-acetic acid,
(Z)-17α-(N,N-diisopropylcarboxamide)-5α-androst-3-ylidene-acetic acid,
17β-(N-t-butylcarboxamide)-A nor-androst-3-ene-3-carboxylic acid,
17α-(N,N-diisopropylcarboxamide)-5α-androst-3-ene-3-acetic acid, or
17α-(N-t-butylcarboxamide)-5α-androst-2-ene-3-acetic acid.

5. A compound of claim 4 which is 17α-(N-t-butylcarboxamide)-androst-3,5-diene-3-carboxylic acid or a salt thereof.

6. A compound of claim 4 which is 17α-(N-t-butylcarboxamide)-estra-1,3,5(10)-triene-3-carboxylic acid or a salt thereof.

7. A compound of claim 4 which is 17α-(N-t-butylcarboxamide)-5α-androst-1-ene-4-aza-3-ene.

8. A pharmaceutical composition comprising a compound according to claim 1 and a pharmaceutically acceptable carrier.

9. A method of inhibiting steroid 5-α-reductase in mammals that comprises administering to a subject an effective amount of a compound of claim 1.

10. A method of reducing prostate size in mammals that comprises administering to a subject an effective amount of a compound of claim 1.

11. A method of treating prostatic adenocarcinoma in mammals that comprises administering to a subject an effective amount of a compound of claim 1.

12. A process for thee preparation of the α-epimer of 17β-acyl 5α-reductase inhibiting steroidal compounds which comprises reacting said 17β-acyl 5α-reductase inhibiting steroidal compound in a solvent and a base at increased temperatures to form, after isolation and work up, the corresponding α epimer.

13. The process of claim 12 wherein the solvent is ethylene glycol or dimethyl sulfoxide.

14. The process of claim 12 wherein the base is sodium hydroxide or potassium hydroxide.

15. The process of claim 12 wherein the increased temperature is the reflux temperature of the reaction mixture.

16. A process of claim 12 in which the starting 17β-acyl substituent of the starting material is of the formula:

in which A is absent or present as $C_{1-12}$ linear or branched alkylidene; and R is;
i) hydrogen, hydroxyl, $C_{1-8}$ alkyl, hydroxy$C_{1-8}$ alkyl, $C_{1-8}$ alkoxy, $NR^1R^2$ where $R^1$ and $R^2$ are each independently selected from hydrogen, $C_{1-8}$ alkyl, $C_{3-6}$ cycloalkyl or phenyl, or
ii) substituted alkyl, cycloalkyl or aryl where:
a) substituted alkyl is linear or branched $C_1$-$C_{12}$ substituted with one or more substituents selected from the group consisting of: aryl, acyloxy, amino, N-acylamino, oxo, carboxyalkyl, halogen and protected —OH;
b) cycloalkyl is nonaromatic, unsaturated or saturated, cyclic or polycyclic $C_3$-$C_{12}$, optionally containing one or more heteroatoms, and optionally substituted with one or more substituents selected from the group consisting of: aryl, hydroxyalkyl, alkyl, alkoxy, acyloxy, amino, N-acylamino, oxo, carboxyalkyl, halogen and protected —OH; and
c) aryl is cyclic or polycyclic aromatic $C_3$-$C_{12}$, optionally containing one or more heteroatoms, provided that when C is 3 the aromatic ring contains at least two heteroatoms and when C is 4 the aromatic ring contains at least one hetero atom, and optionally substituted with one or more substituents selected from the group consisting of: alkyl, $C_6$-$C_{12}$ aryl, hydroxyalkyl, alkoxy, acyloxy, amino, N-acylamino, nitro, cyano, halogen, carboxyalkyl, —$S(O)_nR^5$, protected —OH, where n is 0–2, and $R^5$ is hydrogen, alkyl, substituted alkyl, cycloalkyl or $C_6$-$C_{12}$ aryl.

17. The ketone reduction product of the compounds of claim 1.

18. The ketone reduction product of the compounds of claim 2 wherein the $C_{17}$ position substituent is of the formula

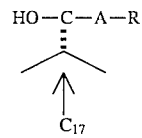

wherein A and R are as described in claim 2.

* * * * *